United States Patent [19]

Bridges et al.

[11] Patent Number: 6,063,025
[45] Date of Patent: May 16, 2000

[54] APPARATUS FOR HOLDING INTESTINES OUT OF AN OPERATIVE FIELD

[75] Inventors: Doye R. Bridges, Victoria, Tex.;
Frederick L. Coe, Santa Barbara, Calif.

[73] Assignee: Bioenterics Corporation, Carpenteria, Calif.

[21] Appl. No.: 09/325,974

[22] Filed: Jun. 4, 1999

Related U.S. Application Data

[60] Continuation-in-part of application No. 09/132,211, Aug. 17, 1998, Pat. No. 5,976,078, which is a division of application No. 08/763,287, Dec. 11, 1996, Pat. No. 5,795,290, which is a division of application No. 08/405,529, Mar. 16, 1995, Pat. No. 5,651,762, which is a continuation-in-part of application No. 08/089,713, Jul. 9, 1993, abandoned.

[51] Int. Cl.[7] ..................................................... A61B 17/00
[52] U.S. Cl. ............................................................. 600/208
[58] Field of Search .................................... 600/201, 206, 600/208, 235, 210; 128/850

[56] References Cited

U.S. PATENT DOCUMENTS

| | | |
|---|---|---|
| 1,213,005 | 1/1917 | Pillsbury . |
| 1,480,680 | 1/1924 | Glover . |
| 1,550,403 | 8/1925 | Turkus . |
| 1,944,009 | 1/1934 | Homer . |
| 2,305,289 | 12/1942 | Coburg . |
| 2,938,519 | 5/1960 | Marco . |
| 3,288,131 | 11/1966 | Garland . |
| 3,364,919 | 1/1968 | Hunnicut . |
| 3,863,639 | 2/1975 | Kleaveland . |
| 3,882,855 | 5/1975 | Schulte et al. . |
| 3,961,629 | 6/1976 | Richter et al. . |
| 4,048,987 | 9/1977 | Hurson . |
| 4,291,687 | 9/1981 | Sinnreich . |
| 4,421,107 | 12/1983 | Estes et al. ............................. 600/206 |
| 4,533,356 | 8/1985 | Bengmark et al. . |
| 4,544,371 | 10/1985 | Dormandy, Jr. et al. . |
| 4,592,339 | 6/1986 | Kuzmak et al. . |

(List continued on next page.)

FOREIGN PATENT DOCUMENTS

| | | |
|---|---|---|
| 536850 | 4/1993 | European Pat. Off. . |
| 2416687 | 10/1979 | France . |
| 797668 | 1/1981 | U.S.S.R. . |

OTHER PUBLICATIONS

Disposable laparotomy sponge and packaging by Kendall Healthcare Products Company, The Kendall Company of Mansfield, Massachusetts © 1990 Kendall (one page).

Brookwalter™ Retractor System distributed by Codman and Shurtleff, Inc. of Randolph, Massachusetts. (one page).

O'Sullivan–O'Connor self–retaining abdominal retractor distributed by Codman and Shurtleff, Inc. of Randolph, Massachusetts. (one page).

Stedman's Medical Dictionary 25th Edition Illustrated, Copyright © 1990, Williams & Wilkins, three cover sheets and pp. 1242–1244 (six pages total).

Poron® S2000 Silicone Data Sheet, Poron® S2000 Silicone Preliminary Product Properties, published by Rogers Corporation of Woodstock, Connecticut (no date) (1 page total).

USP Class VI testing of S2000–80–08250 sponsored by Rogers Corporation of Woodstock, Connecticut (no date) (1 page total).

(List continued on next page.)

*Primary Examiner*—Jeffrey A. Smith
*Attorney, Agent, or Firm*—Akin, Gump, Strauss, Hauer & Feld LLP

[57] ABSTRACT

A nonabsorbent monolithic holding member having a plurality of openings to define spring segments and columns adapted for use within an abdominal cavity of a patient to keep the patient's bowels out of the operative field during open pelvic surgery. The holding member has a peripheral edge formed of a resiliently deformable material sized to be received within the abdominal cavity. The resilient deformation of at least a portion of the peripheral edge of the holding member in combination with the spring segments and columns results in a predetermined residual reactive force against the abdominal cavity to assist in positioning the holding member in the abdominal cavity while resisting movement of the retracted intestines though the deformed openings.

21 Claims, 5 Drawing Sheets

U.S. PATENT DOCUMENTS

| | | |
|---|---|---|
| 4,634,427 | 1/1987 | Hannula et al. . |
| 4,637,377 | 1/1987 | Loop . |
| 4,666,447 | 5/1987 | Smith et al. . |
| 4,777,943 | 10/1988 | Chvapil . |
| 4,848,364 | 7/1989 | Bosman . |
| 4,850,953 | 7/1989 | Haber et al. . |
| 4,889,107 | 12/1989 | Kaufman . |
| 4,931,039 | 6/1990 | Coe et al. . |
| 4,981,465 | 1/1991 | Ballan et al. . |
| 5,059,208 | 10/1991 | Coe et al. . |
| 5,064,433 | 11/1991 | Blom et al. . |
| 5,116,310 | 5/1992 | Seder et al. . |
| 5,207,699 | 5/1993 | Coe et al. . |
| 5,346,484 | 9/1994 | Van Lindert . |
| 5,425,357 | 6/1995 | Moll et al. . |
| 5,460,621 | 10/1995 | Gertzman et al. . |
| 5,520,609 | 5/1996 | Moll et al. . |
| 5,527,264 | 6/1996 | Moll et al. . |
| 5,651,762 | 7/1997 | Bridges . |
| 5,658,298 | 8/1997 | Vincent et al. . |
| 5,795,290 | 8/1998 | Bridges . |
| 5,879,290 | 3/1999 | Bridges et al. . |
| 5,902,247 | 5/1999 | Coe et al. . |
| 5,976,078 | 11/1999 | Bridges ................................ 600/206 X |

OTHER PUBLICATIONS

Mechanical Engineering Design, Third Edition, by Joseph Edward Shigley; Copyright © 1977, 1972, 1963 by McGraw–Hill, Inc.; Chapter 3: Deflection Analysis, title page, © page, and pp. 95, 113, 114 (5 pages total).

Plastazote® Crosslinked LD Polyethylene Foam, Technical Information LD–1, Zotefoams plc., Apr. 1996, (one page).

Health Care Range, Plastzote/Zotefoam Product Examples Lists, (one page) (no date).

Zotefoams' Process for Manufacturing Plastazote®, Evazote®, and Supazote® Crosslinked Closed Cell Polyolefin Foams, Zotefoams plc. Article, (one page) (no date).

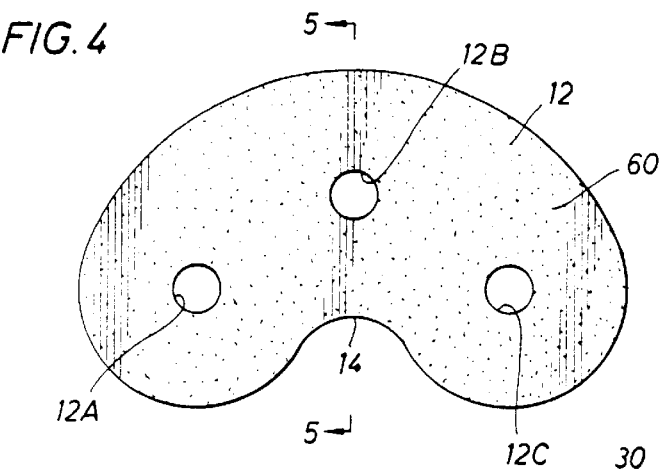
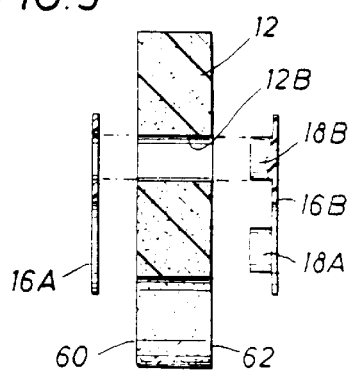
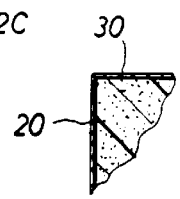
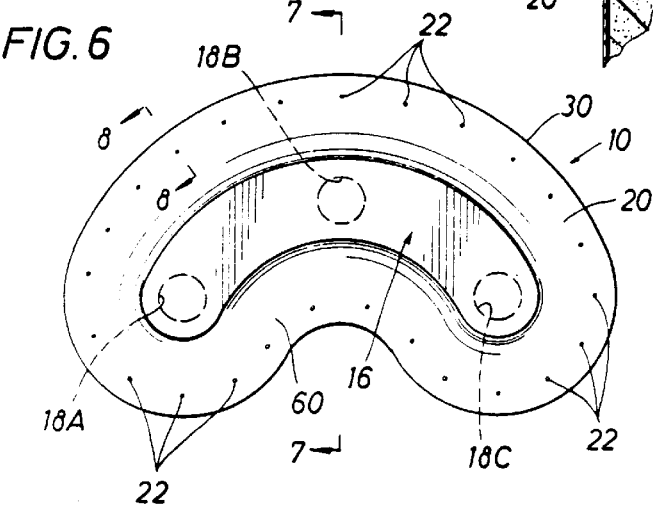
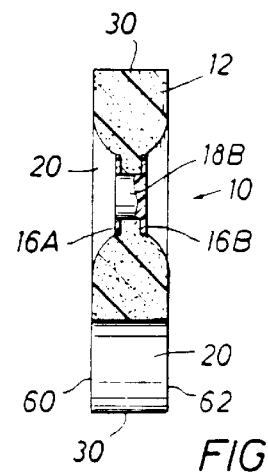
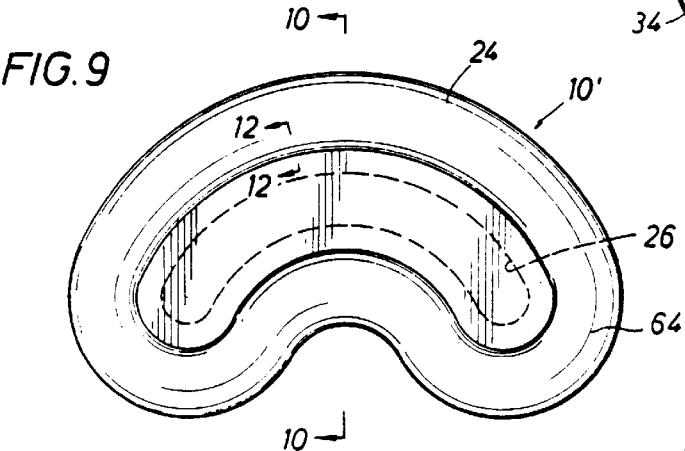
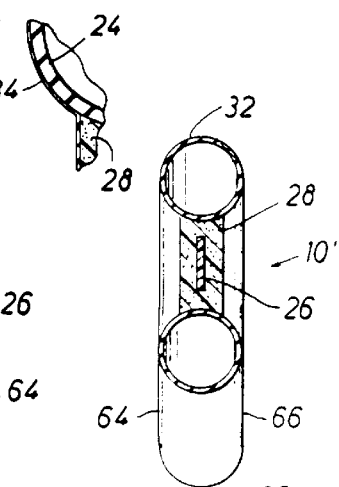

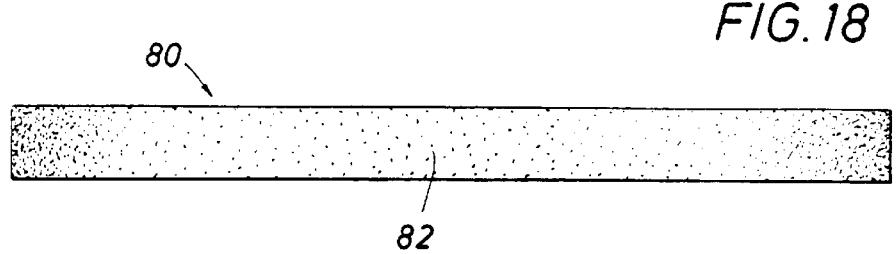
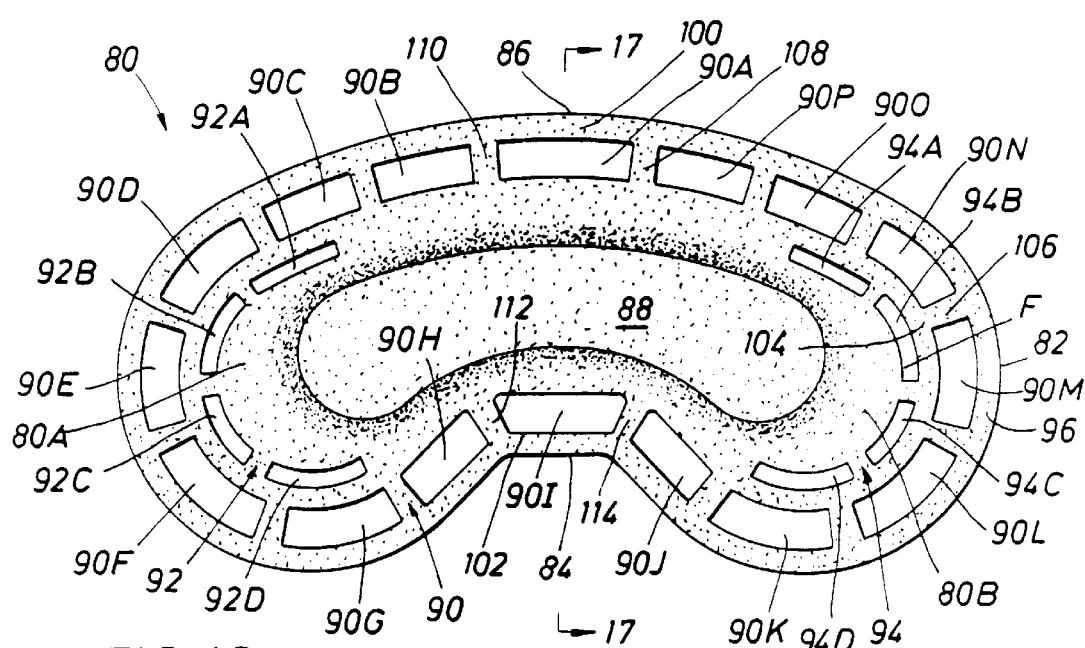
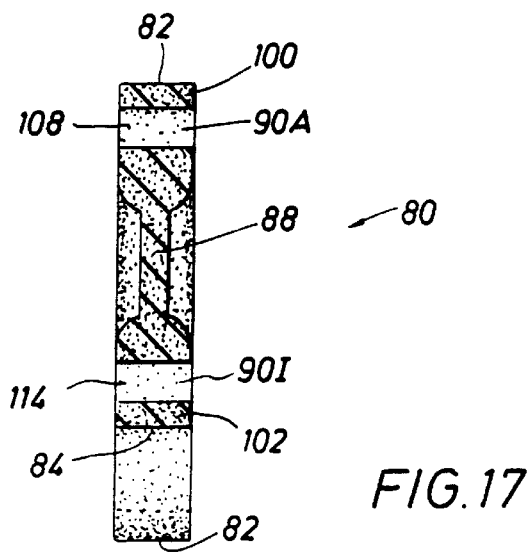

APPARATUS FOR HOLDING INTESTINES OUT OF AN OPERATIVE FIELD

This is a continuation-in-partapplication of Ser. No. 09/132,211 filed Aug. 17, 1998, now U.S. Pat. No. 5,976,078 which is a divisional application of Ser. No. 08/763,287 filed Dec. 11, 1996, now U.S. Pat. No. 5,795,290, which is a divisional application of Ser. No. 08/405,529 filed on Mar. 16, 1995, now U.S. Pat. No. 5,651,762, which is a continuation-in-part application of Ser. No. 08/089,713 filed Jul. 9, 1993, now abandoned.

FIELD OF THE INVENTION

The invention relates to an apparatus for holding intestines out of an operative field. In particular, the invention relates to a nonabsorbent monolithic bean-shaped surgical holding member sized to be received in a patient's abdominal cavity to hold the omentum and intestines out of the operative field during open transabdominal pelvic surgery. An operating procedure for using the holding member is also disclosed.

BACKGROUND OF THE INVENTION

When pelvic surgery is performed trans-vaginally or with a laparoscope there is generally no delay in return of normal motility to the intestines. However, when open pelvic surgery is required, intra-operative bowel (e.g. intestine and omentum) irritation can result.

Peristalsis is successive waves of involuntary contractions passing along the walls of the intestine forcing the contents onward. The absence or reduction of peristalsis following surgery is referred to as post-operative ileus. Ileus results in bloating, cramping, nausea and vomiting as a result of the mechanical and functional obstruction of the intestines during post-operative recovery. This usually increases a hospital stay by twenty-four to forty-eight hours.

Additionally, during open pelvic surgery the surgeon must be careful while holding the intestines out of the operative field so as not to constrict, or worse, cut off proper flow of the patient's vena cava and aorta that provide blood to and from the heart.

The use of devices for retaining and resisting movement of the viscera, or organs, adjoining the field of an abdominal surgical procedure is common surgical practice. Such retaining devices include pads, such as towels or large sponges, such as 4 ply-18"×18" disposable laparotomy sponges supplied by Kendall Healthcare Products Company, the Kendall Company, of Mansfield, Mass. These loose woven cloth sponges are used to pack the omentum and the intestines into the abdominal cavity and are often held in place by a metal retractor blade of sufficient width and depth, such as used with the Weinstein retractor device, the "BOOKWALTER" retractor system, or the O'Sullivan-O'Connor self-retaining abdominal retractor. Both the "BOOKWALTER" and O'Sullivan-O'Connor retractors are distributed by Codman and Shurtleff, Inc. of Randolph, Mass. The O'Sullivan-O'Connor retractor includes two fixed blades, two removable small blades and one large removable blade.

U.S. Pat. Nos. 4,533,356 and 5,346,484 propose surgical devices for internal use during surgical abdominal operations. However, these two surgical devices, like the pads, are fabricated to absorb blood and/or wound fluid. It is the inventors' present belief that a nonabsorbent, as compared to an absorbent, holding member reduces irritation and the resultant post-operative ileus.

A disposable abdominal retracting pad or retractor known by the trade name DISARP is proposed in U.S. Pat. No. 4,889,107 to Kaufman. This retractor is proposed to comprise a flexible flat metal rod having no memory enclosed in urethane plastic foam, in turn, wrapped in an absorbent woven nylon.

U.S. Pat. No. 4,889,107 further proposes an abdominal retractor that comprises a barrier member forming a surgical dam for retaining viscera in an abdominal cavity during surgery. The retractor in the '107 Kaufman patent is proposed to be nonabsorbent and bent to a selected configuration. A core member made from a soft, malleable aluminum or, alternatively, a metal capable of returning to a predetermined shape after being heated to a certain temperature ("Nitinol") is enclosed within the barrier member to retain the barrier member in a selected configuration. A flexible material such as a plastic foam or silicone rubber encloses the core member and both are covered by a material impermeable to the passage of blood, such as silicone rubber, polyvinylchloride or latex. The '107 Kaufman patent also proposes an embodiment where the retractor device 36 is provided with a series of spaced slots 52 to provide added flexibility. (See FIG. 5 and col. 4, lines 3–16 of Kaufman). However, FIG. 5 of Kaufman clearly shows that the slots 52 are provided around the periphery of the device 36, as opposed to openings not in communication with the edge of periphery of the holding member or device.

While U.S. Pat. No. 4,889,107 proposes in FIG. 4 that the side walls and end walls of the barrier member are upright when positioned adjacent to a surgical field in an abdominal cavity, there is no teaching of a fixed presized indentation in the barrier member to provide proper flow through the patient's aorta and vena cava to and from the heart. A fixed presized indentation would relieve the surgeon from physically having to bend the member to a proper configuration. Further, an indentation in the barrier member of U.S. Pat. No. 4,889,107 was not discussed, disclosed or deemed necessary since the barrier member was not contemplated to be positioned within the walls of the abdominal cavity but, as shown in FIG. 4, the rectangular-shaped barrier member is only placed adjacent to a surgical field with the top and end walls free.

A monolithic nonabsorbent holding member adapted to be received in the patient's abdominal cavity and a presized or preshaped indentation to allow proper flow of the patient's aorta and vena cava would be desirable. Also, sized elongated openings in the holding member adjacent to, but not in communication with, the holding member edge to define spring segments supported by columns in the holding member to assist in positioning the holding member in the abdominal cavity for providing a desired holding force to maintain the operative field clear during open pelvic surgery while limiting movement of the omentum and intestines through these sized openings in the holding member would be desirable.

SUMMARY OF THE INVENTION

A nonabsorbent monolithic holding member adapted for use within a patient's abdominal cavity defined by an anterior wall, a posterior wall and two lateral walls to keep the omentum and intestines out of the operative field during open pelvic surgery is provided. The holding member having an edge formed of a resiliently deformable foam is received within the abdominal cavity. The plastic foam core in the monolithic holding member is, advantageously, formed by compression with heat and pressure to increase the density of the foam core. The core, while foldable, is fabricated to provide a memory to return the holding member to its at-rest flat condition or shape independent of external forces, such as, but not limited to, unfolding, uncoiling, unrolling, unbending by the user. A plurality of sized elongated openings positioned between the edge and compressed core define a system of spring segments supported by columns in the holding member to enhance the resilient deformation of at least a portion of the holding member to provide a desired residual reactive force against the abdominal cavity walls. This residual reactive force assists in positioning of the holding member in the abdominal cavity.

Advantageously, a procedure for using the nonabsorbent monolithic holding member to assist in holding intestines within the abdominal cavity defined by the anterior wall, posterior wall and two lateral walls during the open pelvic operation is provided.

BRIEF DESCRIPTION OF THE DRAWINGS

The object, advantages and features of the invention will become more apparent by reference to the drawings which are appended hereto and wherein like letters or numerals indicate like parts and wherein an illustrative embodiment of the invention is shown, of which:

FIG. 4 is a resiliently deformable plastic foam portion of an alternative embodiment of the holding member of the present invention;

FIG. 5 is a section taken along lines 5—5 of FIG. 4 additionally illustrating the alignment of the side plates of the core before assembly;

FIG. 6 is a view similar to FIG. 4 with the side plates assembled and a cover or coating provided over the alternative embodiment of the holding member of the present invention;

FIG. 7 is a section view taken along lines 7—7 of FIG. 6;

FIG. 8 is an enlarged section view taken along lines 8—8 of FIG. 6 to better illustrate the cover or coating for the holding member of the alternative embodiment of present invention;

FIG. 9 is another alternative embodiment of the present invention comprising an inflatable tube;

FIG. 10 is a section view taken along lines 10—10 of FIG. 9;

FIG. 12 is an enlarged section view taken along lines 12—12 of FIG. 9 to better illustrate the cover or coating for the alternative embodiment of the holding member of the present invention;

FIG. 16 is the preferred embodiment of a monolithic holding member of the present invention;

FIG. 17 is a section view taken along line 17—17 of FIG. 16; and

FIG. 18 is bottom view of the holding member of FIG. 16.

DETAILED DESCRIPTION OF PREFERRED EMBODIMENT

Figure 11:
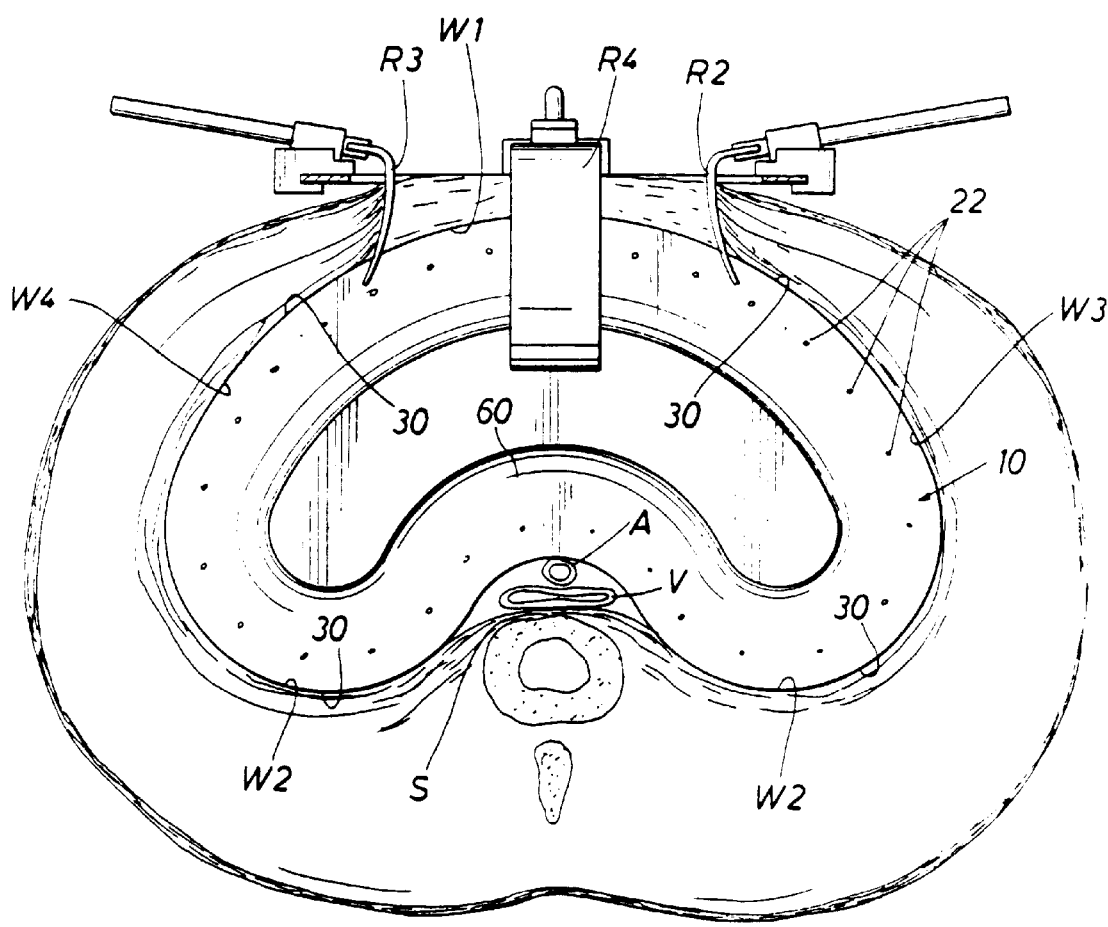
FIG. 11 is an enlarged section view taken along lines 11—11 of FIG. 2 better illustrating the positioning of an alternative embodiment of the present invention between the abdominal cavity walls.

The preferred embodiment of the monolithic holding member, generally indicated at 80 in FIGS. 16, 17 and 18, is sized to be received within the abdominal cavity C of a patient P defined by an anterior wall $W_1$, a posterior wall $W_2$, lateral wall $W_3$ and lateral wall $W_4$, as best shown in FIG. 11. The holding member 80 is preferably a monolithic foam member with a high density core, as will be described below in detail. In alternative embodiments, as shown in FIGS. 2 and 4 to 15, holding members, generally indicated as 10, 10' and 40, are fabricated from a plastic foam and a core, or an inflatable tube having a foam embedded core, as will be described below in detail.

Turning first to FIG. 5, in one alternative embodiment the holding member 10 includes a resiliently deformable plastic foam member 12 having an upper or front surface 60, a lower or rear surface 62, and three bores 12A, 12B and 12C therein. Though three bores are shown in the member 10, a different number of bores could be used. The monolithic plastic foam member 12 is bean-shaped having an overall curved configuration, including an indentation 14. Preferably, the bores are approximately 2.0 centimeters in diameter. The width of each side plate 16A and 16B of the core 16 is approximately 4.5 centimeters. The side plates 16A and 16B are preferably molded from a fairly stiff elastomer, such as a liquid that is injection molded and heat and pressure vulcanized to provide a gum-type material with a memory. Such liquid has been previously supplied as No. 7-6860 by Dow Corning of Midland, Mich. or is now available as Part No. PS1771 by Applied Silicone Corporation of Ventura, Calif.

The three cylindrical connecting members 18A, 18B and 18C are preferably 1 centimeter in length. Upon assembly of side plate 16A with side plate 16B, the foam member 12 is compressed to 1 centimeter. This compression of the foam, the material of which is discussed below, will increase the density of the foam adjacent the central core or side plates 16A and 16B to further protect the patient's aorta A and vena cava V during insertion and use of the holding member. Any suitable adhesive for assembly of connecting members 18A, 18B and 18C to side plates 16A and 16B may be used or common mechanical locking devices for connecting the core 16 together may be used. A preferred adhesive is No. 586 NuSil Medical Grade Adhesive. 1137 by NuSil Silicone Technologies of Carpinteria, Calif.

After the side plates have been assembled, the entire holding member 10 can be coated with a polymer layer or coating 20, such as a dimethyl silicone elastomer, as best shown in FIG. 8. The slippery resultant surface on the front surface 60 and the rear surface 62 of holding member from this elastomer coating allows the bowels to contact and move relative to the holding member without significant friction. This layer 20, as discussed further below, must be soft, compliant, pliable, resiliently deformable and nonporous so that it permits compression of the foam member 12 while being nonabsorbent. This layer 20 may be applied by dipping or spraying onto the foam member 12. Preferably, the holding member is dipcoated by dipping in the coating material for approximately 5 minutes and allowed to air dry for approximately 1 hour then re-dipped for another 5 minutes and again allowed to air dry for approximately another 1 hour. The holding member is then placed into an oven and cured at 300° F. for approximately 3 hours. A coating is Part No. 40,000 medical grade dimethyl silicone elastomer by Applied Silicone Corporation of Ventura, Calif. dispersed in Syxlene.

After the holding member 10 is completely coated, the layer 20 covering the front surface 60 of the holding member 10 could, if desired, be perforated with a plurality of holes 22 to allow air to vent with compression and expansion of the holding member.

As best shown in FIGS. 9 and 10, alternative embodiment holding member 10' having an upper or front surface 64 and a lower or rear surface 66 is constructed of an air filled tube 24, generally having the same overall U-shaped or bean-shaped configuration and dimensions as holding member 80, as discussed below in detail. Though the holding member 10' is shown constructed of one continuous tube, the tube could comprise a plurality of chambers (not shown) strategically placed to prevent inadvertent deflation during an operation. The central core 26 of the member 10' is fabricated from a vulcanized silicone elastomer having a memory, as described above, embedded in a foam 28, such as described below. The foam 28 is in turn attached to tube 24 by a conventional heating process or an adhesive, such as the above-described NuSil-1137 adhesive. As best shown in FIG. 12, the holding member 10' can be dipcoated, as described above, by a soft, flexible, pliable, nonporous and nonabsorbent material 34, such as Applied Part No. 40,000 medical grade dimethyl silicone elastomer or other suitable material.

Figure 15:
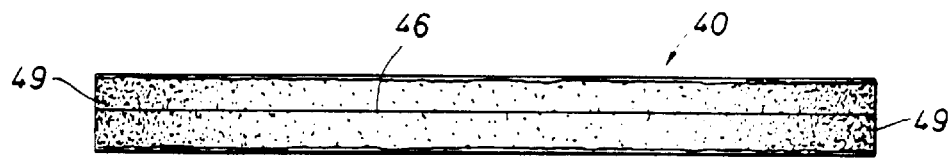
FIG. 15 is a bottom view of the holding member of FIG. 14.
Figure 13:
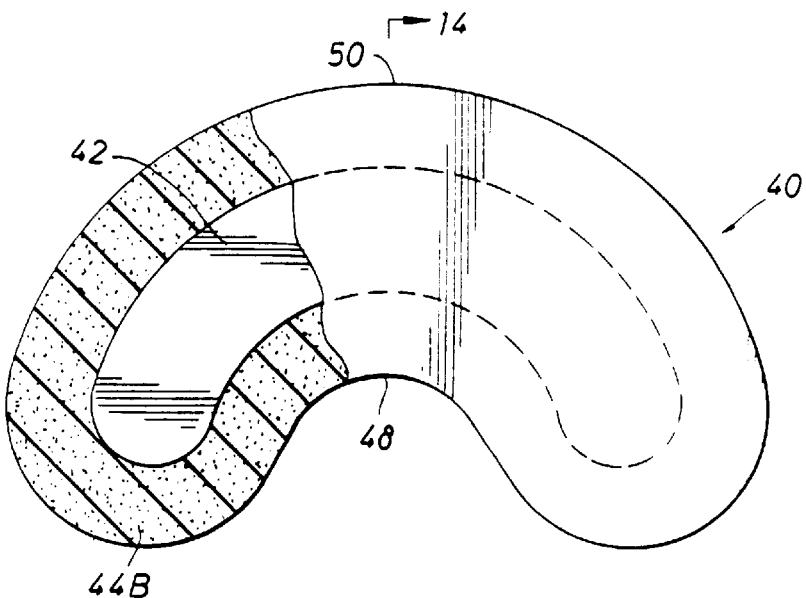
FIG. 13 is another alternative embodiment of the present invention with a portion of the holding member foam and its nonabsorbent cover or coating cut away to better illustrate the core, the remaining portion of the core in the holding member shown in phantom view.
Figure 14:
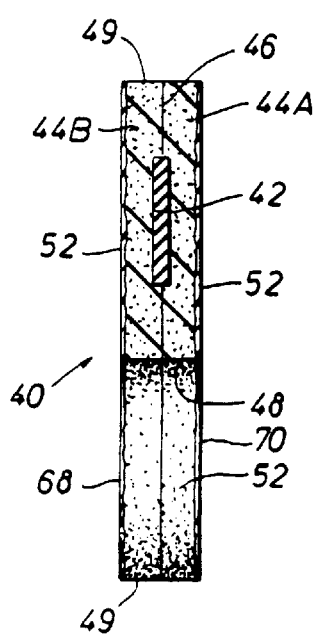
FIG. 14 is a section view taken along lines 14—14 of FIG. 13.

Turning now to FIGS. 13–15, alternative embodiment holding member 40, having an upper or front surface 68, and a lower or rear surface 70, includes a core 42, as best shown in FIGS. 13 and 14, preferably made of a vulcanized silicone elastomer, previously available from Dow Corning and now available from Applied Silicone Corporation, as described above. This core is centrally embedded in a closed cell foam, as described below, that is nonabsorbent to blood and other body fluids. The foam is cut and provided in two sections 44A, 44B, such as shown in FIG. 14. The vulcanized silicone elastomer core 42 is centrally attached to one of the sections with use of an adhesive, such as the NuSil 1137 adhesive. Preferably, at least 3 centimeters of cellular foam are provided at all points between the peripheral edge of the holding member 40 and the core 42. The other section of the foam is then positioned by the use of adhesive preferably along the full engaging surface 46, including the other side of the core, to provide a unitary one piece holding member. The holding member should then be allowed to cure for 24 hours, trimmed of excess adhesive and cleaned with isopropyl alcohol.

In the alternative embodiment, once the two sections of the foam 44A and 44B are joined by the adhesive with the core therein, the holding member 40 may then be completely dip coated, as described above, with a nonabsorbent layer 52, as best shown in FIG. 14. Preferably, the coating is Part No. 40,000 a medical grade dimethyl silicone elastomer by Applied Silicone Corporation of Ventura, Calif. However, the holding member 40 would be nonabsorbent without the coating because of the use of a closed cell foam. While the front surface 68 and the rear surface 70, though the member 40 is a mirror image along its centerline, of the foam cut from the sheet will have a smooth surface, the edge will have a rougher surface because of the foam cells. Upon coating, the front surface 68 and the rear surface 70 will become slippery and the edge will still have a sufficiently rough surface to provide engagement with the abdominal cavity walls.

Turning now to FIGS. 16–18, the preferred embodiment of the monolithic uncoated holding member 80 includes a plurality of elongated openings. In particular, the holding member 80 preferably includes a first row, generally indicated at 90, of sixteen (16) elongated openings 90A, 90B, 90C, 90D, 90E, 90F, 90G, 90H, 90I, 90J, 90K, 90L, 90M, 90N, 90O and 90P between the core 88 and the edge 86 of the holding member 80. A second row, generally indicated at 92, 94, of elongated openings are also preferably provided between the first row 90 of openings and the core 88 on the lateral sides 80A, 80B, respectively, of the holding member 80. In particular, elongated openings 92A, 92B, 92C, 92D are provided on one lateral side 80A of the holding member 80, and elongated openings 94A, 94B, 94C, 94D are provided on the other lateral side 80B of the holding member 80. The second row 92, 94 of openings along with the first row 90 of openings provide the desired residual reactive force in the resiliently deformable material, as will be described below. In particular, these elongated openings are positioned in the monolithic holding member fabricated from a preferred foam material, as described below, in combination with the high density core 88 formed by compression with heat and pressure. Preferably, the core 88 is compressed to approximately ⅓ of the distance of the edge 82. In this case, where the edge is 2.1 centimeters the core thickness is approximately in the range of 0.8 to 0.9 centimeters.

The core 88 is fabricated, after being folded, to return to its memory or at-rest flat, position, as shown in FIG. 16, and has a durability rating of 100 cycles. In particular, the openings 90A and 90I are positioned along the centerline, defined by line 17—17 of FIG. 16, to facilitate in the folding of the holding member 80. The spring segments 100, 102, along with the high density core 88, assist in returning the holding member 80 to its flat position. Indentation 84 in combination with the opening 90I defining the spring segment 102, openings 90H and 90J and columns 112 and 114 provide a holding member that is designed not to provide a pressure over 20 millimeters of mercury on the patient's aorta or vena cava at a 3 millimeter deflection.

The elongated openings shown in FIG. 16 are generally to scale, where opening 90A has a length of approximately 4.3 centimeters and a height (along line 17—17 of FIG. 16) of approximately 1.3 centimeters. The trapezoidal shaped opening 90I has a length at its top side of approximately 4.3 centimeters and its bottom side of approximately 3.5 centimeters and a height of approximately 1.3 centimeters. The second row 92, 94 of openings have a height of approximately 0.6 centimeters. The maximum distance that the edge 82 should deform is in the range of 2 to 3 centimeters, that would flatten the edge 82 adjacent opening 90M of side 80B, approximately to the point F, as shown in FIG. 16. Also, the distance from the edge 82 at 86 to the bottom of opening 90A is approximately 2 centimeters, so that this maximum compression would push the edge 82 at 86 in compression with the high density core 88. As can now be seen, these plurality of openings in the rows 90, 92, 94 provide a system of spring segments and columns to allow the holding member 80 to accommodate a wide variety of cavity openings while limiting movement of the omentum and intestines into the operative field during open transabdominal pelvic surgery.

A preferred medium size holding member 80 would include a center height from the top of the indentation 84 to the top of the holding member 80 at 86 of approximately 10.0 centimeters. The overall length of the holding member 80 at the tangential intersection at 84 is approximately 26.0 centimeters. The overall height of the holding member 80 is approximately 14.0 centimeters with a thickness of approximately 2.1 centimeters. This 14.0 centimeter overall height and 10.0 centimeter holding member height provides 4.0 centimeters between the indentation 84 about the patient's aorta and vena cava to the bottom of the holding member.

While the alternative embodiment holding member 10, as shown in FIGS. 4–8, alternative embodiment holding member 10', shown in FIGS. 9 and 10, and alternative embodiment holding member 40, shown in FIGS. 13–15, have the same general bean-shaped configuration and dimensions of the preferred holding member 80, the holding members 10, 40 and 80 have squared off peripheral edges 30, 49 and 82, respectively, while the holding member 10' has a radiused or curved peripheral edge 32. However, it is to be understood that the holding members 10, 40 and 80 could be fabricated with a radiused, curved, combination radiused and flat peripheral edge or other geometric combination shaped edge.

Though not shown in the preferred embodiment, the holding member 80 of FIGS. 16, 17 and 18 could alternatively have a rigid core, such as core 16, relocated on one or both of an outside surface(s) of the core 88 of the holding member 80 to provide a more positive engagement surface between the retractor blade $R_4$ and the holding member 80. Additionally, while the retractor blade $R_4$ could engage the compressed foam core 88 to position the holding member 80 in the patient's cavity, a positive attachment device could be provided between the retractor blade $R_4$ and the core of any of the disclosed holding members; such as a keyhole in the core and a corresponding key member on the retractor blade $R_4$.

The white plastic foam member 80 is preferably fabricated from a polyethylene foam available from Zotefoam Co. of Croyden, Surrey CR9 3AL, England under the trademark "PLASTAZOTE LD-18," though could be fabricated from other comparable medical grade polymers or materials. Other possible materials that could be used for the holding member could include those disclosed in U.S. Pat. Nos. 2,938,519; 3,863,639; 4,637,377; 4,777,943; 4,889,107; 4,981,465 and 5,795,290, which are incorporated by references herein for all purposes.

Preferably, the holding member 80 is formed by molding. In particular, an approximately 2.54 centimeter sheet of the white "PLASTAZOTE LD-18" foam, as described above, is preheated in an oven at approximately 320° F. The sheet of foam is then shuttled into a cool molding area and the tops and bottoms of the molds are compressed with approximately ten (10) tons of pressure. After the compressed foam is cooled in the mold, the top and bottom molds are then retracted and the holding member removed from the press. A steel rule die is then aligned with the molded holding member. The steel rule die and the "PLASTAZOTE LD-18" compressed foam is then shuttled into a die cutting press. The pressed steel rule die then cuts the holding member and the steel rule die and die cut holding member are removed from cutting press.

The rough edges are trimmed and the die cut areas removed from the molded and die cut holding member. Finally, the holding member is wrapped, packaged and terminally sterilized by gas or gamma radiation. As now can be seen, the above simple manufacturing process can be used in reducing the cost of manufacture of the holding member 80.

PROCEDURE FOR USE

Turning now to FIGS. 1–3 and 11, the procedure for use of the holding member 80 is shown. During open pelvic surgery, a number of different presized holding members in individual sterile packages will preferably be available to the surgeon. For example, aged patients and smaller patients would use a different sized holding member than that described above for a medium sized patient. However, the overall configurations of these different size holding members can be predetermined by averaging a number of Computerized Axial Tomography (CAT) scan cross sections on the abdominal cavity.

Figure 1:
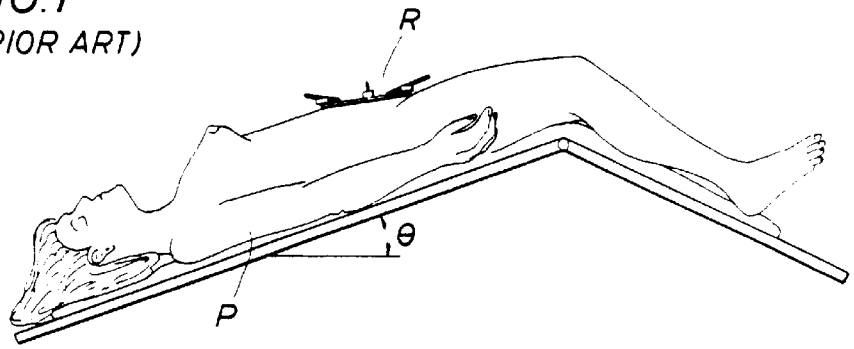
FIG. 1 is an elevational view of the positioning of a conventional retractor on a patient positioned in the "Trendelenburg" position before a holding member of the present invention is inserted in the abdominal cavity.
Figure 3:
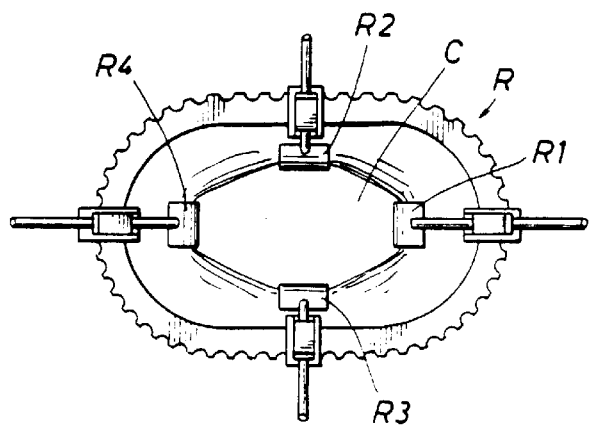
FIG. 3 is a top view of a conventional four-way retractor positioned on the patient as shown in FIGS. 1 and 2.
Figure 2:
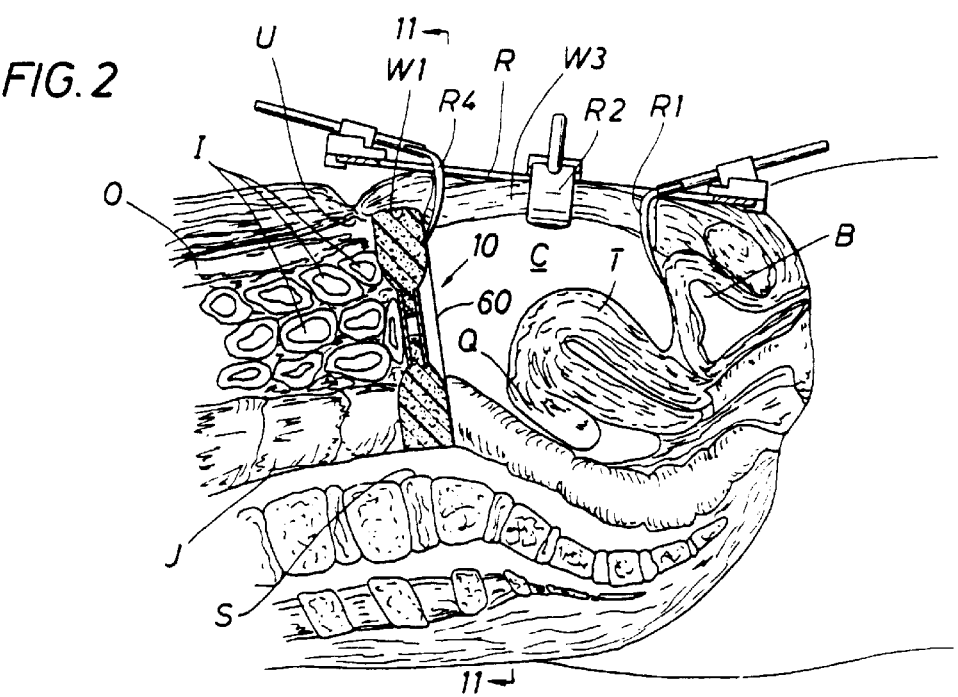
FIG. 2 is an enlarged cross section elevational view of the patient's abdominal cavity with a holding member inserted between the anterior wall adjacent the umbilicus and the posterior wall around a patient's vena cava and aorta.

As best shown in FIGS. 2 and 3, an incision is used to open the pelvic area of the patient P. A lower midline incision, lower transverse incision or any other medically acceptable opening may be used. After retracting the abdominal walls $W_3$ and $W_4$ with blades $R_2$ and $R_3$, respectively, using a conventional 4-way retractor, such as the "BOOKWALTER" retractor R, as shown in FIGS. 1–3 and 11, the urinary bladder B is retracted with a suitably sized lower retractor blade $R_1$. The vertical distance between the sacral spine S and the umbilicus U or anterior wall $W_1$ adjacent the umbilicus U is then measured. This measurement is used to select the proper size holding member.

Prior to insertion of the holding member, the patient P is placed momentarily into an extreme "Trendelenburg" position allowing the intestines I and omentum O along with the colon J to recede into the upper abdomen as much as possible. FIG. 1 illustrates the basic "Trendelenburg" position, though the angle 0 could be larger as desired by the surgeon. The holding member 80 is then folded in half along its centerline, as discussed above, and moved through the incision into the abdominal cavity C. If desired, using the concave portion of the holding member 80, defined by the core 88, as a scoop, the intestines I are moved further upwards in the upper abdomen until the member 80 is positioned at or preferably 2 centimeters below the umbilicus U. The surface of the holding member 80 in contact with the intestines is preferably concave to centrally locate the intestines.

The holding member 80 will preferably have a cross section of an additional 2 to 3 centimeters of distance in all directions for the desired average relaxed abdominal cavity, except, of course, at the indentation 84. The spring segments and columns, as discussed above, in this 2 to 3 centimeters distance allow for compression and variations of cavity contours and sizes. Therefore, the openings in the first row 90 will be reduced in size when the holding member 80 is deformed by the pressure of the patient's abdominal walls.

The anterior and lateral abdominal walls of an average patient can withstand considerable pressure from the inside or tension loading during surgery. However, as best shown in FIG. 11, the patient's aorta A and vena cava V above the spine S in the center of the posterior wall $W_2$ should be protected from a pressure of more than about 15–20 millimeters of mercury. Since the core 88 of the holding member 80 is constructed of a compressed high density foam, such as described above, the holding member will transmit pressure to all the abdominal walls. The core, however, should not come into contact with the patient's aorta A and vena cava V. Of course, the density of the foam increases as the foam is compressed to the core 88.

After the holding member 80 has been inserted, which should only take 1 or 2 minutes, the patient P is repositioned to a more supine or horizontal position to reduce pressure on the patient's diaphragm. As a precaution, it is recommended that the patient's pulse be checked in the common iliac arteries after insertion of the holding member and one finger inserted between the patient's aorta and vena cava and the holding member indentation 84 to be sure that pressure on the vena cava and aorta is not enough to obstruct flow. As a backup, if there is a reduction in venus return, the anesthetist would observe significant tachycardia.

In the alternative, the holding members as shown in the FIGS. can be sized so that minimal or no pressure is exerted on the abdominal walls with the holding member acting merely as a blocking member used in combination with the abdominal cavity walls to keep the intestines out of the operative field.

The fourth or upper blade $R_4$ of the retractor R can then moved into the incision and positioned adjacent the core 88 of the holding member 80 to hold the intestines I and omentum O in the upper abdomen clear of the operative field on the uterus T and/or ovary Q. After completing the intra-abdominal phase of the surgery, the holding member is folded and then removed along with the 4-way retractor and the incision is closed in the usual manner.

The foregoing disclosure and description of the invention are illustrative and explanatory thereof, and various changes in the size, shape and materials, as well in the details of the illustrated construction may be made without departing from the spirit of the invention.

We claim:

1. Apparatus adapted for use within an abdominal cavity of a patient, said cavity defined by an anterior wall, a posterior wall and lateral walls, said apparatus comprising:
   a holding member adapted to be received in the patient's abdominal cavity and having an edge fabricated from foam, and
   at least one opening in said holding member not in communication with said edge.

2. Apparatus of claim 1 where said edge of said holding member is sized to extend beyond the cross-section of the patient's relaxed abdominal cavity.

3. Apparatus of claim 1 wherein said edge of the holding member is flat.

4. Apparatus of claim 1 wherein said holding member having an indentation.

5. Apparatus of claim 4 wherein an opening is disposed in said holding member adjacent to said indentation to reduce pressure on the patient's aorta and vena cava.

6. Apparatus of claim 1 wherein said holding member having a compressed core fabricated by application of heat and pressure to a portion of said holding member.

7. Apparatus of claim 6 wherein openings are positioned above and below said core along a centerline of said holding member to facilitate folding of said holding member along said centerline.

8. Apparatus of claim 1 wherein a plurality of elongated openings are disposed adjacent said edge of said holding member.

9. Apparatus of claim 8 wherein said openings define spring segments and columns.

10. Apparatus of claim 8 wherein said plurality of opening are disposed in at least two rows adjacent to a portion of said edge.

11. Apparatus adapted for use within an abdominal cavity of a patient, said cavity defined by an anterior wall, a posterior wall and lateral walls, said apparatus comprising:
    a monolithic holding member fabricated from a material and adapted to be received in the patient's abdominal cavity and having an edge and a core, wherein said material of said core has a higher density than said edge; and
    at least one opening in said holding member not in communication with said edge.

12. Apparatus of claim 11 wherein said material is foam.

13. Apparatus of claim 11 wherein said holding member having a presized indentation.

14. Apparatus of claim 11 wherein said holding member having a core fabricated by application of heat and pressure to a portion of said monolithic holding member.

15. Apparatus of claim 11 wherein a plurality of elongated opening are disposed in said holding member between said edge and said core.

16. Apparatus of claim 15 wherein said openings define spring segments and columns.

17. Apparatus of claim 15 wherein said plurality of openings are disposed in at least two rows adjacent to a portion of said edge to define spring segments and columns to provide a predetermined compressability of said holding member.

18. Apparatus adapted for use within an abdominal cavity of a patient, said cavity being defined by an anterior wall, a posterior wall and lateral walls, said apparatus comprising:
    a monolithic holding member adapted to be received in the patient's abdominal cavity having an edge fabricated from foam and having a core, and
    at least one opening in said holding member not in communication with said edge to define a spring segment.

19. Apparatus of claim 18 wherein said holding member having an indentation wherein said opening is disposed in said holding member adjacent to said indentation to reduce pressure on the patient's aorta and vena cava.

20. Apparatus adapted for use within an abdominal cavity of a patient, said cavity defined by an anterior wall, a posterior wall and lateral walls, said apparatus comprising:
    a holding member adapted to be received in the patient's abdominal cavity and having an edge formed of a deformable polymer, said holding member having a compressed core fabricated by application of heat and pressure to a portion of said holding member, and
    at least one opening in said holding member not in communication with said edge.

21. Apparatus adapted for use within an abdominal cavity of a patient, said cavity defined by an anterior wall, a posterior wall and lateral walls, said apparatus comprising:
    a holding member adapted to be received in the patient's abdominal cavity and having an edge formed of a deformable polymer, a plurality of elongated openings are disposed adjacent said edge of said holding member, said openings define spring segments and columns, and
    at least one opening in said holding member not in communication with said edge.

* * * * *